(12) United States Patent
Heeps et al.

(10) Patent No.: US 8,128,642 B2
(45) Date of Patent: Mar. 6, 2012

(54) FLUID DELIVERY SYSTEM FOR SURGICAL INSTRUMENTS

(75) Inventors: Andrew Heeps, Kensington, CT (US); Jon Wojculewicz, Bristol, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 512 days.

(21) Appl. No.: 12/427,792

(22) Filed: Apr. 22, 2009

(65) Prior Publication Data

US 2009/0275902 A1 Nov. 5, 2009

Related U.S. Application Data

(60) Provisional application No. 61/049,820, filed on May 2, 2008.

(51) Int. Cl.
*A61B 17/10* (2006.01)

(52) U.S. Cl. ............ 606/142; 606/151; 24/542; 227/19; 227/175.1

(58) Field of Classification Search .................... 16/87.2; 24/30.5 L, 573.09, 456, 6, 517, 542; 132/144, 132/112, 217, 223–226, 159–161, 245, 251, 132/260, 264, 273, 275–284; 227/175.1, 227/108, 181.1, 151, 19, 175.3; 424/422, 424/423, 433, 451, 454; 604/265, 164.01–164.09, 604/285; 606/120, 139, 142, 151, 157, 148, 606/158, 205–209, 214–215, 221
See application file for complete search history.

(56) References Cited

U.S. PATENT DOCUMENTS

| 565,698 | A | * | 8/1896 | Sparks ............................... 24/25 |
| 1,982,207 | A | * | 11/1934 | Furniss .......................... 606/148 |
| 3,757,387 | A | * | 9/1973 | Bush et al. .................. 166/241.7 |
| 4,345,600 | A | * | 8/1982 | Rothfuss ........................ 606/148 |
| 4,394,864 | A | * | 7/1983 | Sandhaus ........................ 128/843 |
| 4,412,370 | A | * | 11/1983 | Speirs .............................. 24/268 |
| 5,411,481 | A | * | 5/1995 | Allen et al. .................... 606/144 |
| 5,584,856 | A | * | 12/1996 | Jameel et al. .................. 606/220 |
| 5,649,938 | A | * | 7/1997 | Allen et al. .................... 606/144 |
| 5,749,893 | A | | 5/1998 | Vidal et al. |
| 5,843,098 | A | * | 12/1998 | Allen et al. .................... 606/144 |
| 5,843,126 | A | * | 12/1998 | Jameel ........................... 606/220 |
| 5,954,259 | A | | 9/1999 | Viola et al. |

(Continued)

FOREIGN PATENT DOCUMENTS

EP 2039308 A2 3/2009

(Continued)

OTHER PUBLICATIONS

European Search Report for EP 09251238.3-2310 date of completion is Aug. 18, 2009 (3 pages).

*Primary Examiner* — Ryan Severson
*Assistant Examiner* — David Eastwood (57) ABSTRACT

There is provided a penetratable toothed fastener for clamping tissue during surgery. The toothed fastener includes first and second legs each having longitudinal rows of transverse teeth and a securing member configured to pass through the transverse teeth to hold first and second legs closed relative to each other and about tissue. A locking mechanism is provided to retain the securing member within the first and second legs of the toothed fastener. The toothed fastener additionally includes receptacles for the receipt of medicant materials and holes in the teeth to dispense the materials to clamped tissue.

17 Claims, 7 Drawing Sheets

U.S. PATENT DOCUMENTS

| | | | |
|---|---|---|---|
| 5,989,215 | A | 11/1999 | Delmotte et al. |
| 6,488,197 | B1 | 12/2002 | Whitman |
| 7,238,195 | B2 | 7/2007 | Viola |
| 2003/0149439 | A1 * | 8/2003 | Wendlandt .................... 606/151 |
| 2006/0100649 | A1 | 5/2006 | Hart |
| 2007/0078414 | A1 * | 4/2007 | McAllister et al. ........... 604/272 |
| 2008/0039879 | A1 | 2/2008 | Chin et al. |

FOREIGN PATENT DOCUMENTS

FR 2632833 A1 * 12/1989

* cited by examiner

FLUID DELIVERY SYSTEM FOR SURGICAL INSTRUMENTS

CROSS-REFERENCE TO RELATED APPLICATIONS

The present application claims priority to U.S. Provisional patent application No. 61/049,820, filed May 2, 2008 the disclosure of which is hereby incorporated by reference herein.

BACKGROUND

1. Technical Field

The present disclosure relates to a fluid delivery system for surgical instruments. More particularly, the present disclosure relates to a fastener for releasing treatment material to clamped tissue.

2. Background of Related Art

During certain surgical procedures as is often necessary to clamp tissue, such as, vascular tissues, to prevent leakage therethrough during surgeries. The procedure typically involves placing clips or clamps within an applicator device and applying the clamps to the tissue on one side of an area, for example a diseased section of vascular tissue or colonic tissue, and placing another set of clamps on the opposing side of the diseased section. Thereafter, the diseased section can be excised and the resulting free ends of the tissue reattached.

During surgery certain problems may arise. For example, manipulation of surrounding tissue, as well as fluid pressure within the tissue, may cause loosening of the clamp and resulting leakage or even possible detachment of the clamp. Additionally, it is often desirable to provide certain medicament or treatment materials such as, for example, biomechanical mediums or antimicrobials solutions to the tissues during the surgery.

Therefore, it is desirable to provide a mechanical fastening device having a securing mechanism for maintaining the fastening devices in a closed position during the surgery. It is further desirable to provide a mechanical fastening device capable of applying medicament or treatment materials to the tissues during the surgery.

SUMMARY

There is disclosed a toothed fastener for securing tissue. The toothed fastener generally includes an upper leg and a lower leg, each of the upper and lower legs having a row of teeth, each tooth having a proximal face and a distal face. The toothed fastener further includes a longitudinally extending securing member. A hole of predetermined diameter is formed in each of the proximal and distal faces and is of sufficient size to allow passage of the securing member therethrough. The upper or lower legs are movable from an open position to a closed positions placing all the holes in longitudinal alignment such that the securing member can pass through all the holes in the teeth of the upper and lower legs.

In a specific embodiment, each tooth has a pair of spaced apart holes formed in each of the distal and proximal faces. In this embodiment, the securing member has first and second legs for passage through the pair of spaced apart holes. The securing member includes a backspan such that the first and second legs extend distally from the backspan.

In one embodiment, the hole formed in the distal face of the distal most tooth is sized to engage the securing member in a friction fit fashion.

In a particular embodiment, each of the teeth are hollow or define a receptacle for receipt of material such that passage of the securing member through the holes of the teeth releases the material into the space between the first and second legs. The material may be contained within a puncturable capsule.

In the disclosed toothed fastener each leg has a base, each base having an opening to the interior of the tooth for passage of material into the tooth. A membrane is provided covering the openings in each leg to retain the material within the teeth.

In one embodiment, a connector is affixed to a proximal end of each of the first and second legs. In a specific embodiment, the connector is a living hinge. In a more specific embodiment, the living hinge is formed integrally with the proximal ends of the first and second legs.

There is also disclosed a system for applying a fastener to tissue including an applicator having a first and a second jaw and a toothed fastener positionable within the first and second jaws. The toothed fastener includes an upper leg and a lower leg, each of the upper and lower legs having a row of transverse, longitudinally extending teeth, each tooth having a proximal face and a distal face. The toothed fastener also includes a longitudinally extending securing member. A hole of predetermined diameter is formed in each of the proximal and distal faces and is of sufficient size to allow passage of the securing member therethrough. The upper or lower legs are movable from an open position spaced apart to a closed position substantially adjacent each other placing all the holes in longitudinal alignment such that the securing member passes through all the holes in the teeth of the upper and lower legs. The first and second jaws of the applicator are operable to move the upper and lower legs between the open and closed positions.

In one embodiment of the system, each tooth has a pair of spaced apart holes formed in the proximal and distal faces and the securing member is a staple bar having a backspan and first and second legs extending distally from the backspan. The first and second legs being configured to pass through the pairs of spaced apart holes to secure the upper and lower legs in the closed position.

The applicator further includes a pusher, engageable with the backspan of the staple bar, to drive the staple bar distally relative to the toothed fastener.

The present disclosure contemplates a fluid delivery system having an actuating handle assembly, a pair of jaws operably connected to the handle assembly, the pair of jaws each having teeth defining openings, and a puncturing member receivable in the openings of the teeth, the teeth defining at least one receptacle containing a fluid. In certain embodiments, the pair of jaws includes a first jaw and a second jaw arranged for clamping onto tissue. The fluid may be a medicament, tissue sealant or tissue adhesive. The fluid may be disposed in a puncturable capsule, the securing member having a tip for puncturing the puncturable capsule.

The present disclosure contemplates a tissue fastener having a first leg and a second leg pivotably connected to one another, the first leg and second leg each having teeth defining openings, and a securing member receivable in the openings of the teeth. A surgical instrument for applying the tissue fastener to tissue includes a pair of jaws and a handle assembly operably arranged to move the jaws between a closed position for clamping tissue and an open position for releasing the tissue. The jaws of the instrument are arranged to receive the tissue fastener and securing member. The surgical instrument includes a pusher for advancing the securing member through the openings in the teeth of the fastener. The teeth may define at least one receptacle containing a fluid. The fluid may be a medicament, tissue sealant or tissue adhesive.

In a further aspect, a toothed fastener comprises an upper leg and a lower leg, each of the upper and lower legs having a row of transverse longitudinally extending teeth, each tooth having a proximal face and a distal face; a longitudinally extending securing member; and a hole of predetermine diameter formed in each of the proximal and distal faces. The upper or lower legs are movable from an open position spaced apart to a closed position wherein all of the holes are in longitudinal alignment enabling the securing member to pass through the holes to maintain the fastener in the closed position.

In certain embodiments, each of the teeth are hollow for receipt of material such that the material is released into spaces defined between the upper and lower legs. The material may be contained within a puncturable capsule. Each of the upper and lower legs may have a base, each base having an opening to the interior of the tooth for passage of material into the tooth. In certain embodiments, a membrane covering the openings in each leg to retain the material within the teeth.

DESCRIPTION OF THE DRAWINGS

Various embodiments of the presently disclosed toothed fastener are disclosed herein with reference to the drawings, wherein.

DETAILED DESCRIPTION OF EMBODIMENTS

Embodiments of the presently disclosed fluid delivery system will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
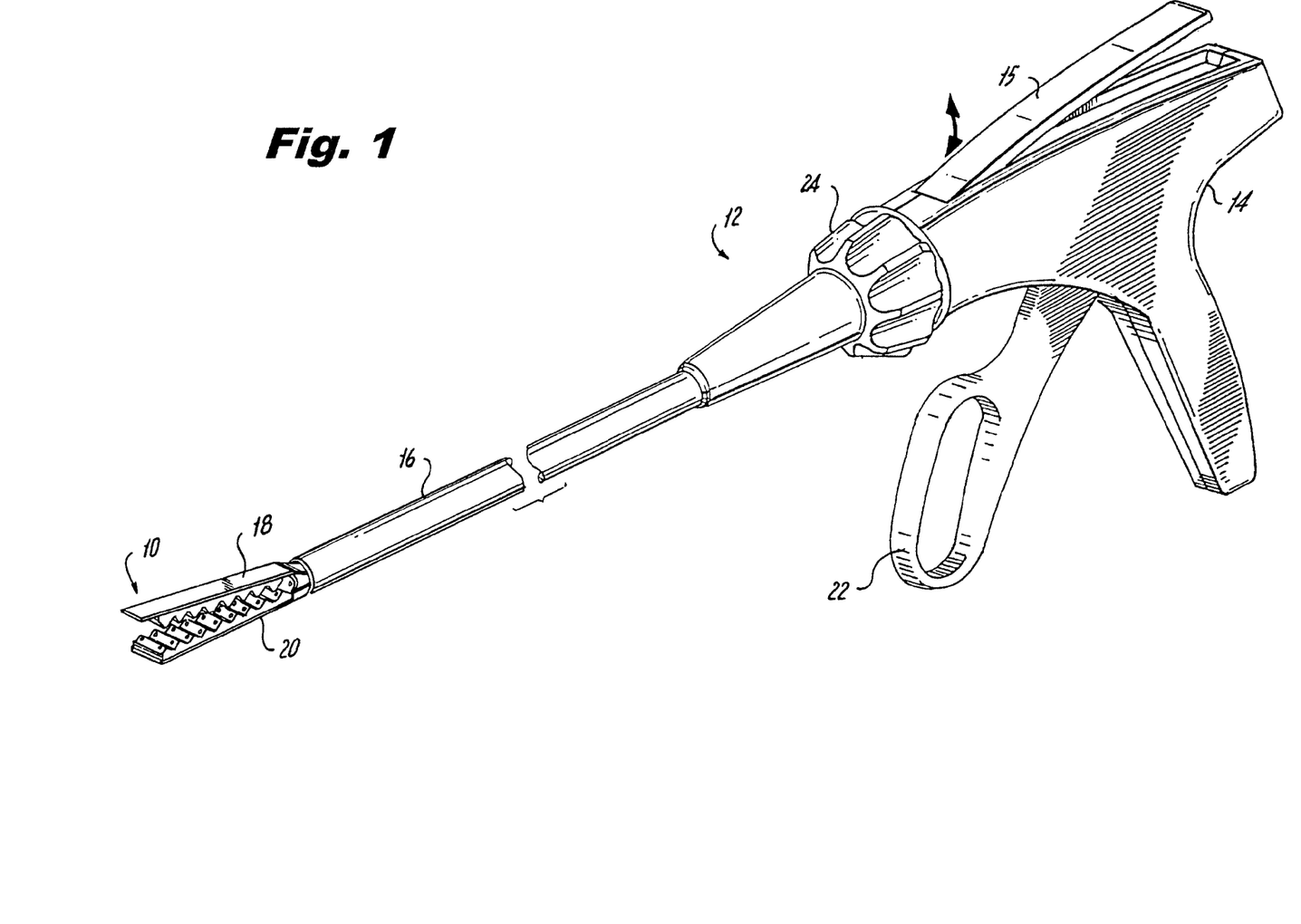
FIG. 1 is a perspective view of one embodiment of a toothed fastener and applicator instrument.

Referring to FIG. 1 there is disclosed a toothed fastener for use in a surgical instrument 12. Surgical instrument 12 can be of the type for open surgery or laparoscopic surgery. In the present disclosure, surgical instrument 12 generally includes a handle 14 having an elongate tubular member 16 extending distally from handle 14. The surgical instrument has an end effector at a distal end of the tubular member 16, including an upper jaw 18 and a fixed jaw 20 that are movable with respect to one another. An actuator or trigger 22 is movably mounted on handle 14 and is operable to drive a securing and puncturing mechanism of fastener 10 into position as described in detail herein below. The handle 14 has a clamping handle 15 for moving the upper and lower jaws 18 and 20 to clamp tissue therebetween. Surgical instrument 12 additionally includes a rotation collar 24, affixed to elongate tubular member 16, to orient upper and lower jaws 18 and 20 during surgery.

Figure 2:
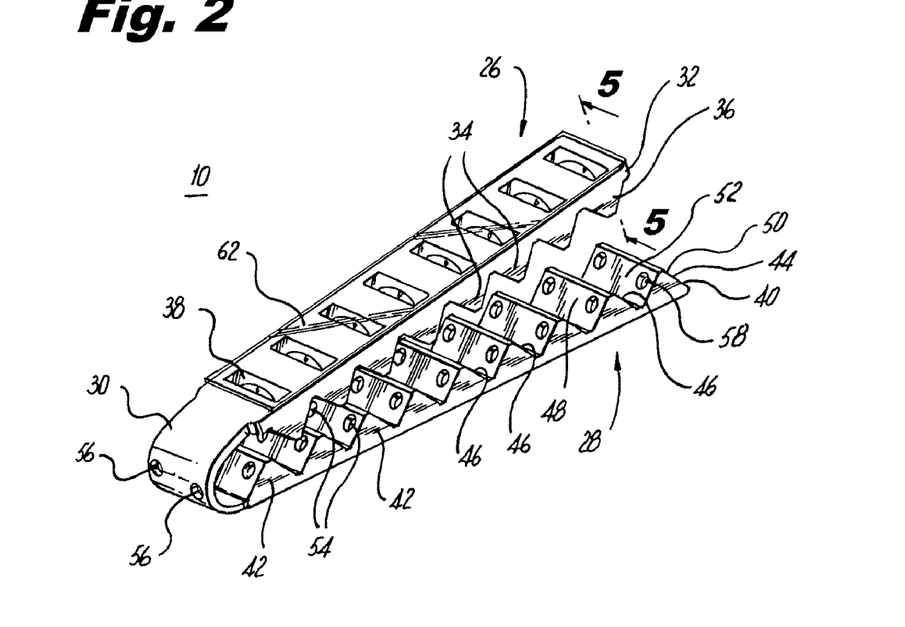
FIG. 2 is a perspective view of the toothed fastener of FIG. 1.

Referring now to FIG. 2, fastener 10 generally includes an upper leg 26 and a lower leg 28. In this embodiment, upper leg 26 and lower leg 28 are connected by a flexible, living hinge 30. Living hinge 30 allows upper leg 26 and lower leg 28 to move between an open position substantially spaced apart to a closed position wherein upper leg 26 is substantially adjacent to lower leg 28. Upper leg 26 generally includes a base 32 having a row of transverse teeth 34 extending lengthwise along base 32. The teeth 34 are hollow so as to define a receptacle in each tooth. Upper leg 26 additionally includes a distal most tooth 36 (or differ slightly to incorporate a locking mechanism as described in more detail herein below). Base 32 includes a plurality of base openings 38 that communicate with a corresponding receptacle in a corresponding tooth, and distal most tooth 36. Openings 38 are provided to receive materials to be dispensed to tissue as described in more detail herein below.

Lower leg 28 also includes a base 40 having a row of transverse teeth 42. The teeth 42 are also hollow so as to define a receptacle in each tooth. Lower leg 28 also includes a distal most tooth 44 on base 40. It should be noted here in that, while the following specific descriptions of configurations, features and/or components of legs 26 and 28 may be given with respect to one of legs 26 and 28, legs 26 and 28 may have the same or different configurations, features and components and are identical in all respects. Teeth 42 of lower leg 28 each include a distal face 46 and proximal face 48. Similarly, distal most tooth 44 includes a distal face 50 and a proximal face 52. Pairs of holes 54 are provided through distal face 46 and proximal face 48 of hollow teeth 42. Living hinge 30 is also provided with a pair of holes 56 which are similar in size and spacing to holes 54. Additionally, in a particular embodiment, distal most tooth 44 has a pair of spaced apart holes 58 in proximal face 52. Distal face 50 of distal most tooth 44 as a pair of spaced apart holes 60 which can differ from holes 54 and 58 in size and may form part of a locking mechanism as described in more detail herein below. In the alternative, holes 60 may be similar to holes 54 and 58 and the pair of spaced apart holes in a distal face of distal most tooth 36 in upper leg 26 may differ from the pairs of spaced apart holes in teeth 34 to form the disclosed locking mechanism.

Upper leg 26 may be provided with a longitudinally extending membrane 62 which serves to cover base openings 38 and secure materials within hollow teeth 34 and 36.

Figure 3:
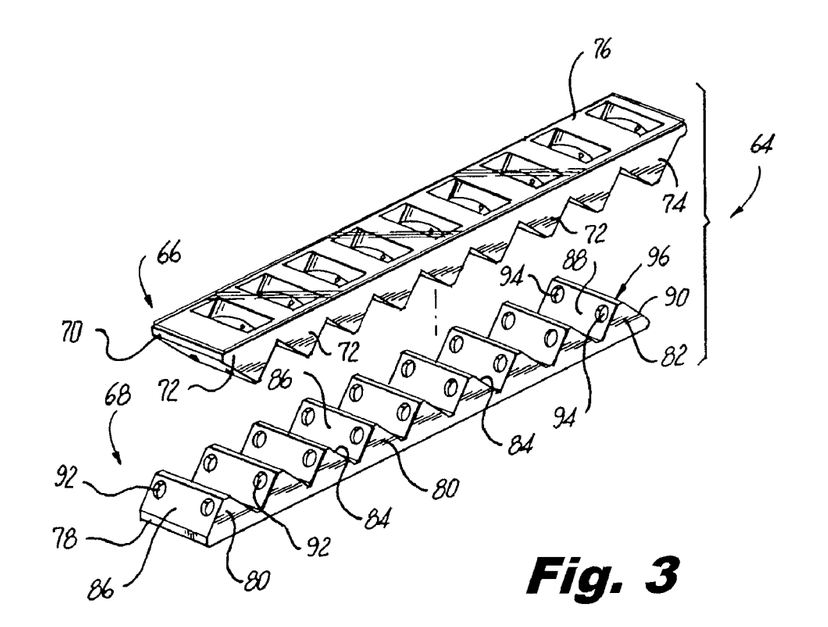
FIG. 3 is a perspective view of an alternative, two part toothed fastener.

Referring for the moment to FIG. 3, there is disclosed an alternative, two-part toothed fastener 64 which is substantially identical to toothed fastener 10 except for the lack of a living hinge. Fastener 64 generally includes an upper leg 66 and a lower leg 68. Upper leg 66 includes a base 70 and a row of transverse, hollow teeth 72. Upper leg 66 also includes a hollow distal most tooth 74. A membrane 76 is provided across base 70 and functions similar to membrane 62 described hereinabove. Similarly, lower leg 68 includes a base 78 having rows of transverse, longitudinally extending hollow teeth 80 and a hollow distal most tooth 82. Each of hollow teeth 80 includes a distal face 84 and a proximal face 86. Hollow distal most tooth 82 also includes a proximal face 88 and a distal face 90. A pair of spaced apart, holes 92 are provided in distal faces 84 and proximal faces 86 of teeth 80. Likewise, proximal face 88 of distal most tooth 82 includes a pair of spaced apart holes 94. In a specific embodiment, distal face 90 includes a pair of spaced apart distal holes 96 which differ in size from holes 94 and 92 and serve as a locking mechanism which functions similar to that which will be described herein below with respect to toothed fastener 10. As shown, upper leg 66 includes a membrane 76. As noted hereinabove, descriptions of the upper and lower legs of the various embodiments of the toothed fastener include similar components, such as the addition of a membrane to lower leg 68, except for variations in distal most tooth 74 and distal most tooth 82. Additionally, the operation of toothed fastener 64, with the exception of a living hinge, functions the same as that described with respect to toothed fastener 10 hereinbelow.

Figure 4:
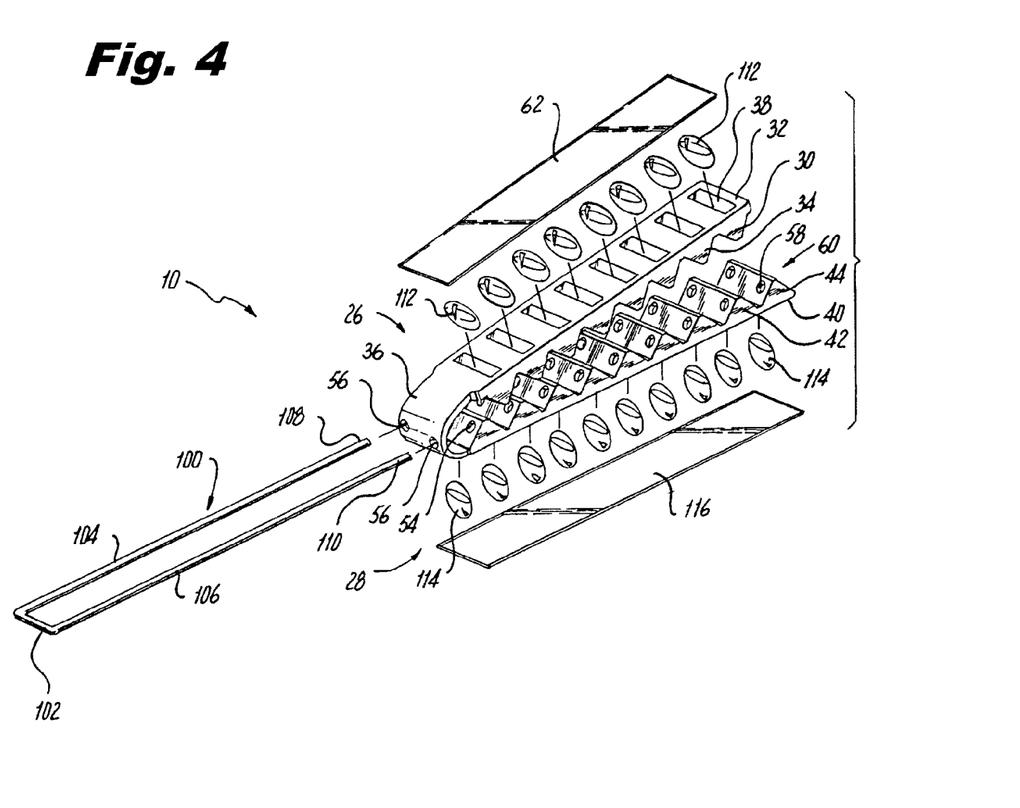
FIG. 4 is a perspective view of the toothed fastener of FIG. 1 with parts separated.

Referring now to FIG. 4, toothed fastener 10 also includes a securing member 100 which serves several functions. Securing member 100 has a backspan 102 and a pair of legs 104 and 106 extending distally from backspan 102. Legs 104 and 106 terminate in distal tips 108 and 110. Securing member 100 is provided to secure upper leg 26 and lower leg 28 in the closed position. Specifically, in the closed position, holes provided in teeth 34 and 36 of upper leg 26 are in direct longitudinal alignment with holes 54, 58 and 60 in lower leg 28. Thus, by driving securing member 100, and specifically legs 104 and 106, distally through holes 56 in backspan 30 and through holes 54, 58 and 60 in lower leg 28 and the corresponding holes in upper leg 26, upper leg 26 is secured in the closed position relative to lower leg 28. Additionally, as tips 108 and 110, of legs 104 and 106, passed through the holes of the teeth as described herein, tips 108 and 110 puncture capsules of material, such as capsules 112 in upper leg 26 and capsules 114 (FIG. 4) in lower leg 28, to release materials contained therein onto tissue captured between upper leg 26 and lower leg 28. Capsules 112 and 114 may contain a variety of materials for treatment or joining of tissue, such as, for example, biomedical mediums, antimicrobial solutions, etc. Materials disclosed in WO 2006/044800, the disclosure of which is hereby incorporated by reference herein, may be used. Lower leg 28 is provided with a membrane 116 to secure capsules 114 within hollow teeth 42 and 44. Finally, tips 108 and 110, in conjunction with smaller diameter holes 60 in distal face 50 of distal most tooth 44, may act as a locking mechanism to prevent staple bar 100 from "backing out of" upper leg 26 and lower leg 28 as described below. The leg 104 and leg 106 may be sized to functionally engage the interior surface of the fastener teeth inside holes 60, or the leg 104 and/or leg 106 have a textured surface for engaging inside the holes 60, or both.

Figure 5:
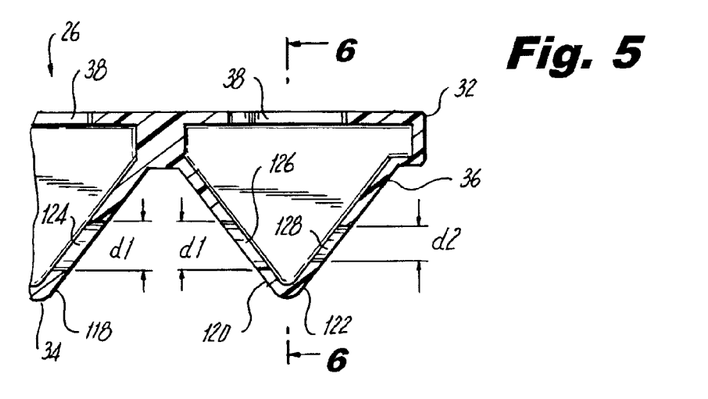
FIG. 5 is a side sectional view taken along line 5-5 of FIG. 2.
Figure 6:
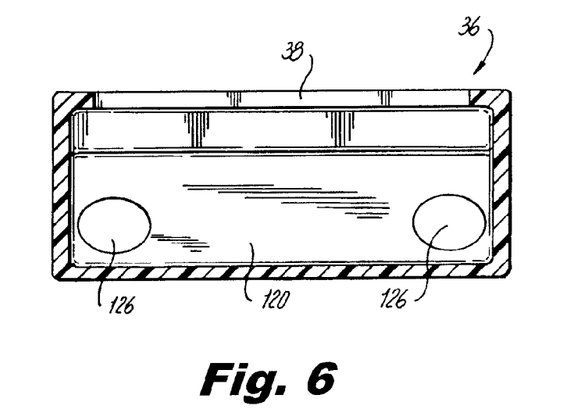
FIG. 6 is an end sectional view taken along line 6-6 of FIG. 5.
Figure 7:
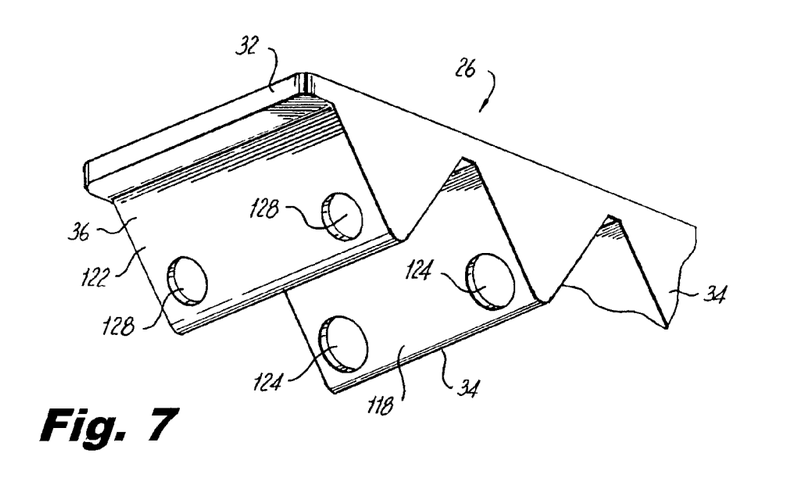
FIG. 7 is a perspective view of the distal end of one leg of the toothed fastener of FIG. 1.

Referring now to FIGS. 5-7, the details of teeth 34 and 36 of upper leg 26 will now be described. As noted hereinabove, upper leg 26 includes a distal face 118 of teeth 34 and proximal and distal faces, 120 and 122, respectively, of teeth 36. Teeth 34 include holes 124 which are similar in size to holes 54 in teeth 42 of lower leg 28. Similarly, distal most tooth 36 includes a pair of spaced apart holes 126 formed in proximal face 120 which are also substantially the same as holes 54. Distal face 122 of distal most tooth 36 includes a pair of spaced apart holes 128 which, together with tips 108 and 110 of securing member 100, may form a locking mechanism to secure staple bar 102 within upper and lower legs 26 and 28. Specifically, holes 124 and 126 may have a diameter d1 which is greater than the diameter d2 of pair of holes 128 in distal face 122 of distal most tooth 36. Diameter d1 of holes 124 and 126 are sized to be greater than the diameter of legs 104 and 106 of staple bar 100 so as to allow materials released from capsules 112 and 114 into the space between upper leg 26 and lower leg 28 in the closed position. Diameter d2 of pair of holes 128 may be sized so as to grasp tips 108 and 110 of staple bar 100 in friction fit fashion thereby locking staple bar 100 in position within upper leg 26 and lower leg 28. The teeth of upper leg 26 define receptacles for a fluid material. The lower leg 28 has teeth defining receptacles and holes that are similar to those discussed above.

Figure 8:
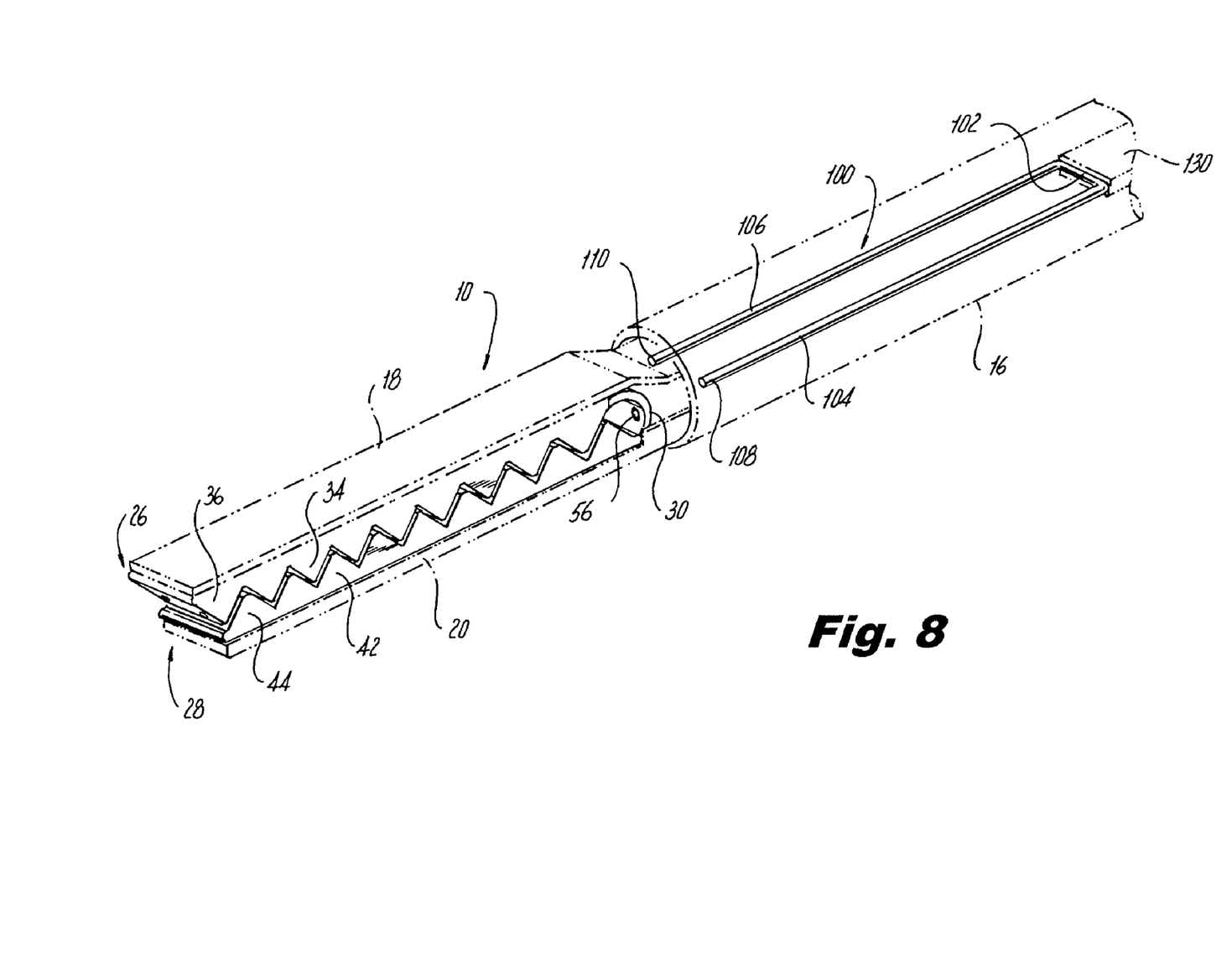
FIG. 8 is a perspective view of the toothed fastener of FIG. 1 in an initial position on the applicator.

Referring now to FIGS. 1 and 8-12, the use of toothed fastener 10 in applicator 12 will now be described. As shown in FIG. 1, toothed fastener 10 is attached to jaws 18 and 20 of applicator 12, such as, for example, by a snap-fit. Once jaws 18 and 20 have been properly positioned around tissue (not shown), clamp handle 15 can be actuated to initially move the jaws to the closed position relative to one another. As best shown in FIG. 8, this brings upper leg 26 into close cooperative alignment with lower leg 28. In this position, teeth 34 of upper leg 36 interengage or interdigitate with teeth 42 of lower leg 28. Depending upon the longitudinal orientation of upper leg 26 relative to lower leg 28 within upper jaw 18 and lower jaw 20, one of distal most tooth 36 of upper leg 26 or distal most tooth 44 of lower leg 28 will become a distally most extending tooth of toothed fastener 10. It should be noted that, depending upon which distal most tooth 36 or 44 becomes the distally most extending tooth, that tooth may be provided with holes of the smaller diameter d2 in the distal face thereof to secure securing member 100. Securing member 100 is in a proximal most position within elongate tubular member 16. Applicator 12 is provided with a pusher 130 positioned against backspan 102 of securing member 100.

Figures 9, 10:
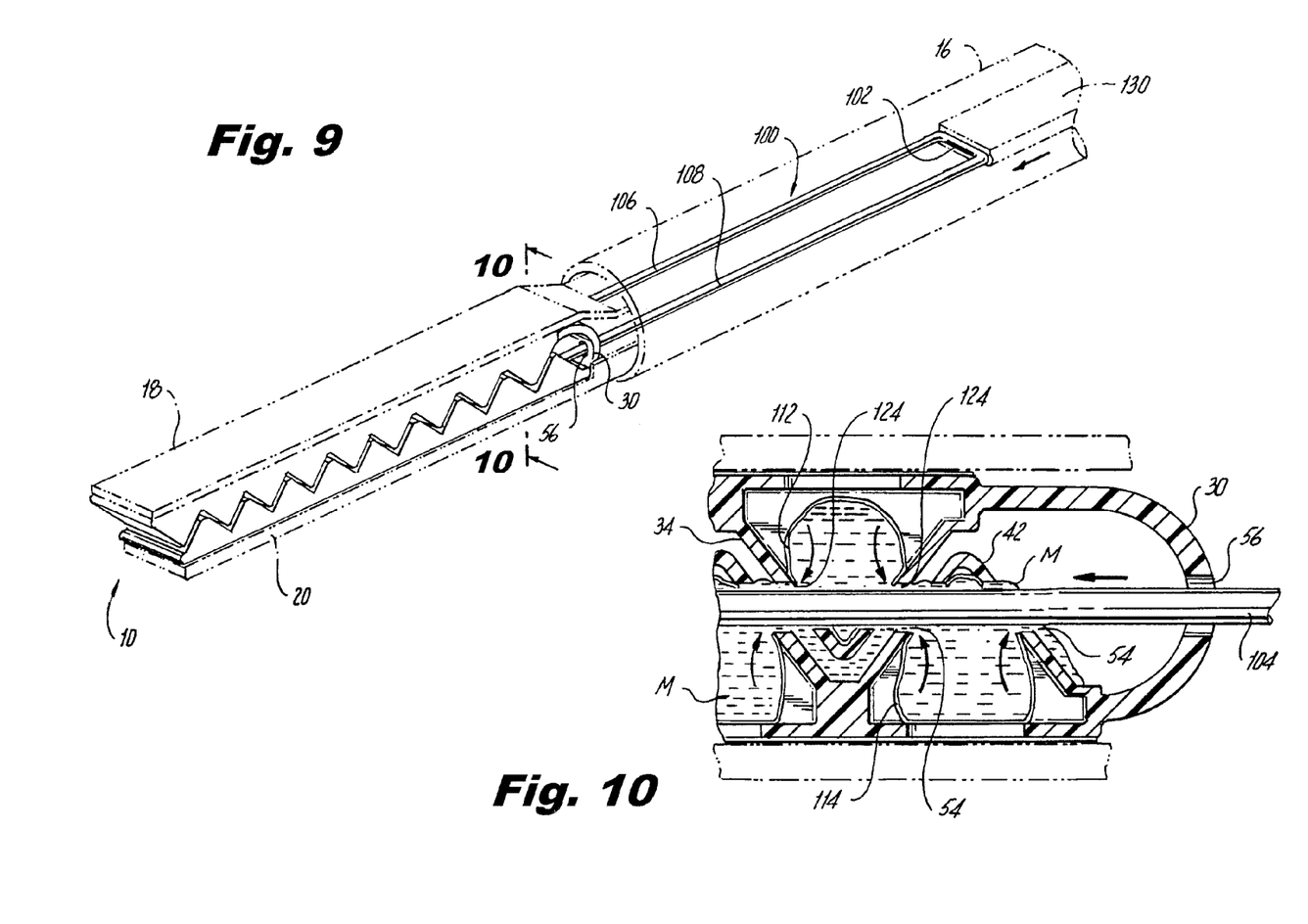
FIG. 9 is a perspective view similar to FIG. 8 during initial puncturing and securement.
FIG. 10 is a side sectional view taken along line 10-10 of FIG. 9.

Referring now to FIG. 9, as trigger 22 is actuated, pusher 130 urges securing member 100 distally within elongate tubular member 16. As securing member 100 moves distally, tips 108 and 110 of legs 104 and 106 pass through holes 56 in living hinge 30. Referring specifically to FIG. 10, as legs 104 and 106 (not shown) moves distally tips 108 and 110 passed through holes 54 in teeth 42 of lower leg 28 and holes 124 of teeth 34 of upper leg 26. As legs 104 and 106 pass through holes 54 and 124, tips 108 and 110 of legs 104 and 106 penetrate or puncture capsules 112 and 114 of material M thereby releasing material M into the spaces defined between teeth 42 and 34. In this manner, toothed fastener 10 is capable of delivering material M to tissues captured between upper leg 26 and lower leg 28. Additionally, the passage of legs 104 and 106 through holes 54 and 124 serve to secure upper leg 26 in the closed position relative to lower leg 28.

Figures 11, 12:
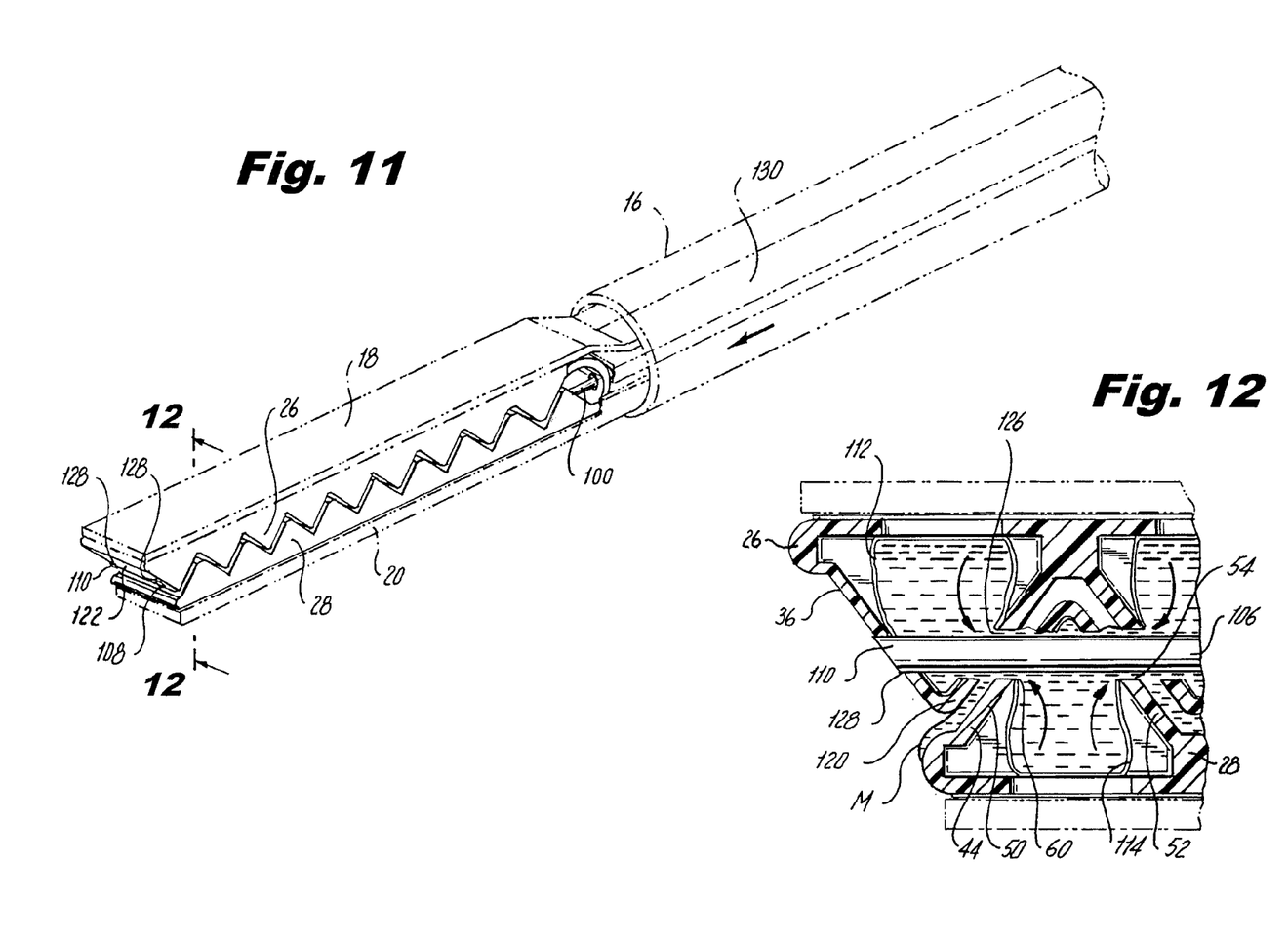
FIG. 11 is a perspective view of the toothed fastener during final puncturing and securement.
FIG. 12 is a side sectional taken along line 12-12 of FIG. 11.

Referring now to FIGS. 11 and 12 and initially with regard to FIG. 11, as pusher 130 advances securing member 100 completely through upper leg 26 and lower leg 28, tips 110 and 108 passed through holes 128 in distal face 122 of distal most tooth 36. As noted hereinabove, holes 128 may have a diameter d2 which is sufficiently small to engage tips 110 and 108 in friction fit fashion. In this manner, securing member 100 is "locked" into position within upper or lower legs 26 and 28, respectively, thereby preventing staple bar 100 from inadvertently pulling out of upper and lower legs 26 and 28. Additionally, the friction fit of tips 110 and 108 within holes 128 serves to seal holes 128 against any leakage of material M therethrough.

Referring to FIG. 12 as leg 106 passes through holes 126 in proximal face 120, capsule 112 is punctured and material and is released. As shown, when distal most tooth 44 of lower leg 28 is not the distally most extending tooth of tooth fastener 10, holes 60 in distal face 50 are of the same diameter as holes 54 in proximal face 52 to allow passage of material M therethrough as capsule 114 is penetrated. When the jaws of the surgical instrument are released from the tissue, through operation of the clamp handle 15, the toothed fastener is secured onto the tissue, as the securing member 100 is retained in the teeth of upper leg 26 and teeth of lower leg 28. Further, the material has been deployed to the tissue site.

It will be understood that various modifications may be made to the embodiments disclosed herein. For example, the teeth of the legs may be formed with a single hole in each of the proximal and distal faces for receipt of a single bar therethrough. Further, the tips of the staple bar may be enlarged to engage the distal most hole in rivet fashion. Additionally, the holes of the teeth may be covered be a penetratable membrane and the material provided as a fluid within the teeth. Therefore, the above description should not be construed as limiting, but merely as exemplifications of particular embodiments. Those skilled in the art will envision other modifications within the scope and spirit of the claims appended hereto.

The invention claimed is:

1. A toothed fastener comprising:
an upper leg and a lower leg, each of the upper and lower legs having a row of teeth, each tooth having a proximal face and a distal face;
a longitudinally extending securing member; and
a hole of predetermine diameter formed in each of the proximal and distal faces and of sufficient size to allow passage of the securing member therethrough, wherein the upper or lower legs are movable from an open position to a closed position wherein all of the holes are in longitudinal alignment enabling the securing member to pass through the holes in the teeth of the upper and lower legs to maintain the fastener in the closed position;
wherein each of the teeth are hollow and contain a material such that passage of the securing member through the holes of the teeth releases the material into the space between the upper and lower legs.

2. The toothed fastener as recited in claim 1, wherein each tooth has a pair of spaced apart holes formed in each of the distal and proximal faces.

3. The toothed fastener as recited in claim 2, wherein the securing member is a staple bar having first and second legs for passage through the pair of spaced apart holes.

4. The toothed fastener as recited in claim 3, wherein the securing member includes a backspan and the first and second legs extend distally from the backspan.

5. The toothed fastener as recited in claim 1, wherein the hole formed in the distal face of a distal most tooth is sized to engage the securing member in friction fit fashion.

6. The toothed fastener as recited in claim 1, wherein the material is contained within a puncturable capsule.

7. The toothed fastener as recited in claim 1, wherein each of the upper and lower legs has a base, each base having an opening to the interior of the tooth for passage of material into the tooth.

8. The toothed fastener as recited in claim 7, further comprising a membrane covering the openings in each leg to retain the material within the teeth.

9. The toothed fastener as recited in claim 1, further comprising a connector affixed to a proximal end of each of the upper and lower legs.

10. The toothed fastener as recited in claim 9, wherein the connector includes at least one hole for passage of the longitudinally extending securing member.

11. The toothed fastener as recited in claim 9, wherein the connector is a living hinge is formed integrally with the proximal ends of the upper and lower legs.

12. A system for applying a fastener to tissue comprising:
an applicator having a first and a second jaw;
a toothed fastener positionable within the first and second jaws, the toothed fastener including:
a) an upper leg and a lower leg, each of the upper and lower legs having a row of teeth, each tooth having a proximal face and a distal face;
b) a longitudinally extending securing member; and
c) a hole of predetermine diameter formed in each of the proximal and distal faces and of sufficient size to allow passage of the securing member therethrough, wherein the upper and lower legs are movable from an open position to a closed position wherein all of the holes are in longitudinal alignment enabling the securing member to pass through the holes in the teeth of the upper and lower legs, wherein the first and second jaws are operable to move the upper and lower legs between the open and closed positions; and
wherein each tooth has a pair of spaced apart holes formed in the proximal and distal faces and the securing member is a staple bar having a backspan and first and second legs extending distally from the backspan such that the first and second legs pass through the pairs of spaced apart holes to secure the upper and lower legs in the closed position.

13. The system as recited in claim 12, wherein the applicator has a pusher engageable with the backspan of the staple bar to drive the staple bar distally relative to the toothed fastener.

14. A toothed fastener comprising:
an upper leg and a lower leg, each of the upper and lower legs having a row of transverse longitudinally extending teeth, each tooth having a proximal face and a distal face;
a longitudinally extending securing member; and
a hole of predetermine diameter formed in each of the proximal and distal faces, wherein the upper or lower legs are movable from an open position spaced apart to a closed position wherein all of the holes are in longitudinal alignment enabling the securing member to pass through the holes to maintain the fastener in the closed position; and
wherein each of the teeth are hollow and contain a material such that the material is released into spaces defined between the upper and lower legs.

15. The toothed fastener as recited in claim 14, wherein the material is contained within a puncturable capsule.

16. The toothed fastener as recited in claim 14, wherein each of the upper and lower legs has a base, each base having an opening to the interior of the tooth for passage of material into the tooth.

17. The toothed fastener as recited in claim 16, further comprising a membrane covering the openings in each leg to retain the material within the teeth.

* * * * *